(12) United States Patent
Lin et al.

(10) Patent No.: US 8,968,280 B2
(45) Date of Patent: Mar. 3, 2015

(54) DOSE DETERMINATION FOR INDUCING MICROCAVITATION IN RETINAL PIGMENT EPITHELIUM (RPE)

(75) Inventors: Charles P. Lin, Arlington, MA (US); Clemens Alt, Watertown, MA (US); Ho Lee, Daegu (KR)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/145,605

(22) PCT Filed: Jan. 22, 2010

(86) PCT No.: PCT/US2010/021811
§ 371 (c)(1),
(2), (4) Date: Oct. 7, 2011

(87) PCT Pub. No.: WO2010/085650
PCT Pub. Date: Jul. 29, 2010

(65) Prior Publication Data
US 2012/0029490 A1 Feb. 2, 2012

Related U.S. Application Data

(60) Provisional application No. 61/146,750, filed on Jan. 23, 2009.

(51) Int. Cl.
*A61B 18/18* (2006.01)
*A61F 9/008* (2006.01)

(52) U.S. Cl.
CPC ............. *A61F 9/008* (2013.01); *A61F 9/00821* (2013.01); *A61F 2009/00863* (2013.01)
USPC .............................................. 606/4; 606/12

(58) Field of Classification Search
CPC ................................ A61F 9/008–9/009; A61F 2009/008–2009/00897
USPC .......................... 606/4, 5, 6, 10–12; 128/898; 600/398–403
See application file for complete search history.

(56) References Cited

U.S. PATENT DOCUMENTS

| 4,644,948 A | 2/1987 | Lang et al. |
| 4,758,081 A | 7/1988 | Barnes |

(Continued)

FOREIGN PATENT DOCUMENTS

| JP | 2001149403 | 6/2001 |
| WO | WO 99/65431 | 12/1999 |

(Continued)

OTHER PUBLICATIONS

Pollack et al. "Tissue Effects of Subclinical Diode Laser Treatment of the Retina" Arch. Ophthalmol. 1998; 116(12):1633-1639.*

(Continued)

*Primary Examiner* — Lynsey Crandall
*Assistant Examiner* — Nathan J Jenness
(74) *Attorney, Agent, or Firm* — Fish & Richardson P.C.

(57) ABSTRACT

Methods and systems for controlling selective targeting of retinal pigment epithelium (RPE) cells within a treatment region of the RPE. The methods include (a) depositing a selected amount of energy on a test region of the RPE; (b) determining an extent to which microcavitation has occurred in the test region; and (c) on the basis of the determination, either depositing the selected amount of energy on the treatment region, or depositing an increased amount of energy on the test region, and repeating steps (b) and (c).

18 Claims, 11 Drawing Sheets

(56) References Cited

U.S. PATENT DOCUMENTS

| | | | |
|---|---|---|---|
| 4,819,621 A | 4/1989 | Ueberle et al. | |
| 5,029,220 A | 7/1991 | Juday | |
| 5,209,221 A | 5/1993 | Riedlinger | |
| 5,254,112 A | 10/1993 | Sinofsky et al. | |
| 5,302,259 A | 4/1994 | Birngruber | |
| 5,430,509 A | 7/1995 | Kobayashi | |
| 5,459,570 A | 10/1995 | Swanson et al. | |
| 5,549,596 A | 8/1996 | Latina | |
| 5,549,598 A * | 8/1996 | O'Donnell, Jr. | 606/6 |
| 5,549,599 A | 8/1996 | Sumiya | |
| 5,620,437 A | 4/1997 | Sumiya | |
| 5,778,133 A | 7/1998 | Plesko | |
| 5,782,822 A | 7/1998 | Telfair et al. | |
| 5,997,141 A | 12/1999 | Heacock | |
| 6,059,772 A | 5/2000 | Hsia et al. | |
| 6,099,522 A | 8/2000 | Knopp et al. | |
| 6,110,165 A | 8/2000 | Ota | |
| 6,186,628 B1 | 2/2001 | Van de Velde | |
| 6,319,274 B1 | 11/2001 | Shadduck | |
| 6,325,792 B1 | 12/2001 | Swinger et al. | |
| 6,428,532 B1 | 8/2002 | Doukas et al. | |
| 6,610,051 B2 | 8/2003 | Bille | |
| 6,671,043 B1 | 12/2003 | Huettman | |
| 6,706,036 B2 | 3/2004 | Lai | |
| 6,743,221 B1 | 6/2004 | Hobart et al. | |
| 6,887,232 B2 | 5/2005 | Bille | |
| 7,036,516 B1 | 5/2006 | Dees | |
| 7,115,120 B2 | 10/2006 | Lin | |
| 7,354,432 B2 | 4/2008 | Eells et al. | |
| 7,763,017 B2 | 7/2010 | Lin | |
| 7,766,903 B2 | 8/2010 | Blumenkranz et al. | |
| 7,947,036 B2 | 5/2011 | Lin | |
| 8,006,702 B2 | 8/2011 | Lin | |
| 8,187,257 B2 | 5/2012 | Lin | |
| 8,366,704 B2 | 2/2013 | Lin et al. | |
| 2001/0034319 A1 | 10/2001 | McMillan et al. | |
| 2002/0198516 A1 | 12/2002 | Knopp et al. | |
| 2003/0050678 A1 | 3/2003 | Sierra et al. | |
| 2004/0039378 A1 | 2/2004 | Lin | |
| 2004/0102765 A1 | 5/2004 | Koenig | |
| 2004/0176752 A1 | 9/2004 | Alfano et al. | |
| 2005/0021013 A1 | 1/2005 | Visuri et al. | |
| 2005/0197655 A1 | 9/2005 | Telfair et al. | |
| 2006/0074468 A1 | 4/2006 | Neev | |
| 2006/0111697 A1 | 5/2006 | Brinkmann et al. | |
| 2006/0161145 A1 | 7/2006 | Lin et al. | |
| 2006/0259022 A1 | 11/2006 | Lin | |
| 2007/0213693 A1 | 9/2007 | Plunkett | |
| 2008/0259422 A1 | 10/2008 | Lin | |
| 2008/0281306 A1 | 11/2008 | Lin | |
| 2010/0049173 A1 * | 2/2010 | Plunkett et al. | 606/4 |
| 2011/0306919 A1 | 12/2011 | Latina et al. | |
| 2012/0296320 A1 | 11/2012 | Lin et al. | |

FOREIGN PATENT DOCUMENTS

| | | | |
|---|---|---|---|
| WO | WO 01/91661 | 12/2001 | |
| WO | WO 2004/043234 | 5/2004 | |
| WO | WO 2005/065116 | 7/2005 | |
| WO | WO 2007/053701 | 5/2007 | |
| WO | WO 2007/092349 | 8/2007 | |
| WO | WO 2008/049164 A1 * | 5/2008 | A61F 9/008 |
| WO | WO 2009/092112 | 7/2009 | |

OTHER PUBLICATIONS

Clemens Alt. (Aug. 2008). Detection of Intracellular Cavitation during Selective Targeting of the Retinal Pigment Epithelium with a Laser Scanner. (Doctoral Dissertation). Retrieved from ProQuest Dissertations and Theses. (Publication No. [3324371]).*
Lee et al. (Optical detection of intracellular cavitation during selective laser targeting of the retinal pigment epithelium: dependence of cell death mechanism on pulse duration. J Biomed Optics. Nov.-Dec. 2007; 12(6): 064034).*

Framme et al. (Selective Targeting of the Retinal Pigment Epithelium in Rabbit Eyes with a Scanning Laser Beam. Invest. Ophthalmol. Vis. Sci. Apr. 2007 vol. 48 No. 4 1782-1792.).*
Schuele et al. "RPE Damage Thresholds and Mechanisms for Laser Exposure in the Microsecond-to-Millisecond Time Regimen" Invest. Ophthalmol. Vis. Sci. Feb. 2005 vol. 46 No. 2 714-719.*
International Search Report for PCT Application No. PCT/US01/17818, dated Aug. 31, 2001.
International Preliminary Examination Report for PCT Application No. PCT/US01/17818, dated May 27, 2003.
Office Action in U.S. Appl. No. 10/296,417, dated Aug. 11, 2004.
Search Report in European Patent Application No. 01941803.7, dated Feb. 21, 2005.
Office Action in U.S. Appl. No. 10/296,417, dated May 17, 2005.
Office Action in U.S. Appl. No. 10/296,417, dated Dec. 1, 2005.
Office Action in European Patent Application No. 01941803.7, dated May 8, 2006.
Office Action in European Patent Application No. 01941803.7, dated May 29, 2007.
Office Action in U.S. Appl. No. 11/428,018, dated Jun. 4, 2007.
International Search Report and Written Opinion for PCT Application No. PCT/US06/42696, dated Sep. 17, 2007.
International Preliminary Report on Patentability for PCT Application No. PCT/US06/42696, dated May 15, 2008.
Office Action in U.S. Appl. No. 11/428,018, dated Jun. 12, 2008.
Office Action in Canadian Patent Application No. 2,410,962, dated Dec. 19, 2008.
Office Action in U.S. Appl. No. 11/428,018, dated Feb. 9, 2009.
Summons to attend oral proceedings in European Patent Application No. 01941803.7, dated Mar. 26, 2009.
Communication from EPO in European Patent Application No. 01941803.7, dated Jul. 14, 2009.
Office Action in U.S. Appl. No. 11/428,018, dated Aug. 20, 2009.
Office Action in U.S. Appl. No. 12/131,612, dated Oct. 8, 2009.
Office Action in U.S. Appl. No. 12/178,384, dated Oct. 8, 2009.
International Search Report and Written Opinion for PCT Application No. PCT/US2010/021811, dated Jan. 22, 2010.
Office Action in U.S. Appl. No. 12/178,384, dated Aug. 25, 2010.
Office Action in Canadian Patent Application No. 2,410,962, dated Sep. 7, 2010.
Search report in European Application No. 10000476.1, dated Sep. 21, 2010.
Office Action in U.S. Appl. No. 12/131,612, dated Sep. 29, 2010.
Office Action in U.S. Appl. No. 11/263,677, dated Oct. 5, 2010.
Office Action in U.S. Appl. No. 11/263,677, dated Jul. 11, 2011.
International Preliminary Report on Patentability for PCT Application No. PCT/US2010/021811, dated Jul. 26, 2011.
Office Action in Australian Patent Application No. 2006308721, dated Aug. 26, 2011.
English translation of Office Action in Japanese Application No. 2008-538118, dated Sep. 20, 2011.
Search Report in European Patent Application No. 06827308.5, dated May 21, 2012.
Vogel et al., "Cavitation Bubble Dynamics and Acoustic Transient Generation in Ocular Surgery with Pulsed Neodymium:YAG Lasers," *Ophthalmology* 93(10): 1259-1269 (1986).
Juhasz et al., "Time-Resolved Observations of Shock Waves and Cavitation Bubbles Generated by Femosecond Laser Pulses in Corneal Tissue and Water," *Lasers in Surgery and Medicine* 19(1): 23-31 (1996).
Kelly et al., "Microcavitation and Cell Injury in RPE Cells Following Short-Pulsed Laser Irradiation", *SPIE* 2975:174-179 (1997).
Lin et al., "Selective Cell Killing by Microparticle Absorption of Pulsed Laser Radiation", *IEEE J. Sel. Topics Quantum Elect.* 5(4): 963-968 (1999).
Mills et al., *Laser Interaction with Tissue and Cells XV, Proc. SPIE* 5319: 245-251 (2004).
Roach et al., *Journal of Biomedical Optics* 9(5): 1288-1296 (2004).
International Preliminary Report on Patentability and Written Opinion for PCT Application No. PCT/US2009/031599, dated Jul. 20, 2010, 10 pages.
International Search Report and Written Opinion dated Aug. 31, 2009 from International Application No. PCT/US2009/031599, 11 pages.
Office Action issued in European Application No. 09702254.5, dated Aug. 27, 2012, 4 pages.

(56) References Cited

OTHER PUBLICATIONS

Office Action issued in European Application No. 09702254.5, dated Feb. 15, 2012, 5 pages.
Office Action issued in IL Application No. 207,701 on Aug. 25, 2013, 1 page. (English translation only).
Office Action issued in IL Application No. 207,701, dated Jun. 18, 2012, 1 page (English translation only).
Supplementary European Search Report for application No. EP 09702254, dated Dec. 16, 2010, 6 pages.
Office Action in U.S. Appl. No. 12/863,281, dated Sep. 4, 2014.

* cited by examiner

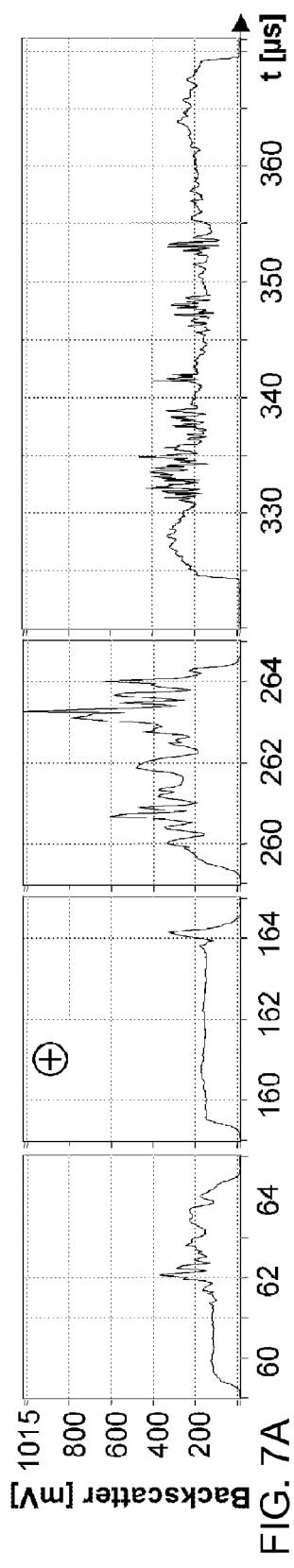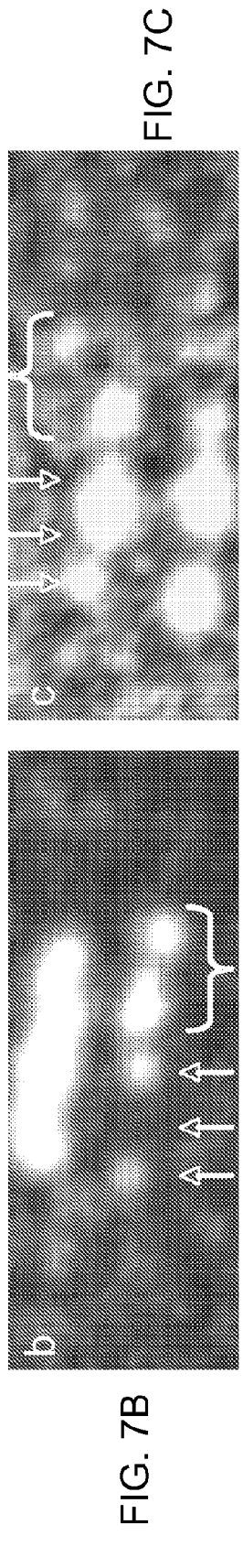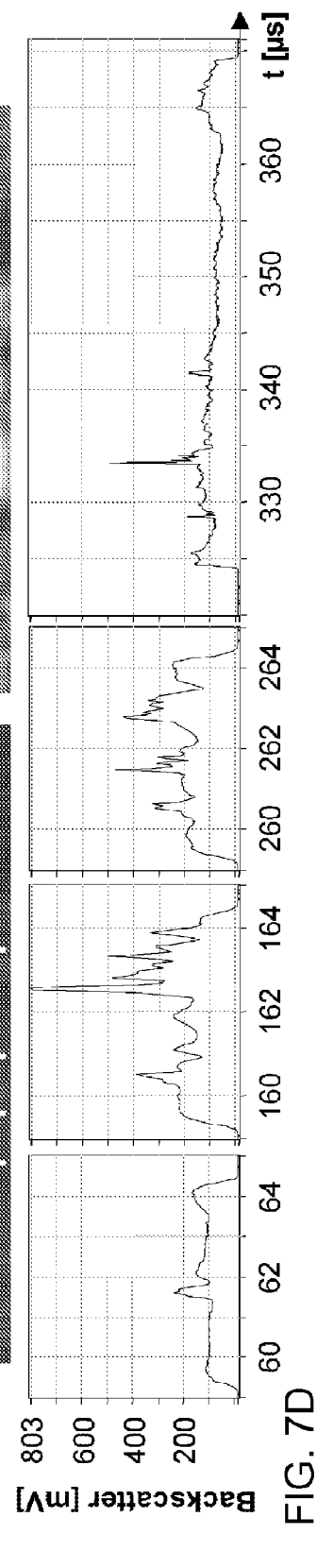
FIG. 7A
FIG. 7B
FIG. 7C
FIG. 7D

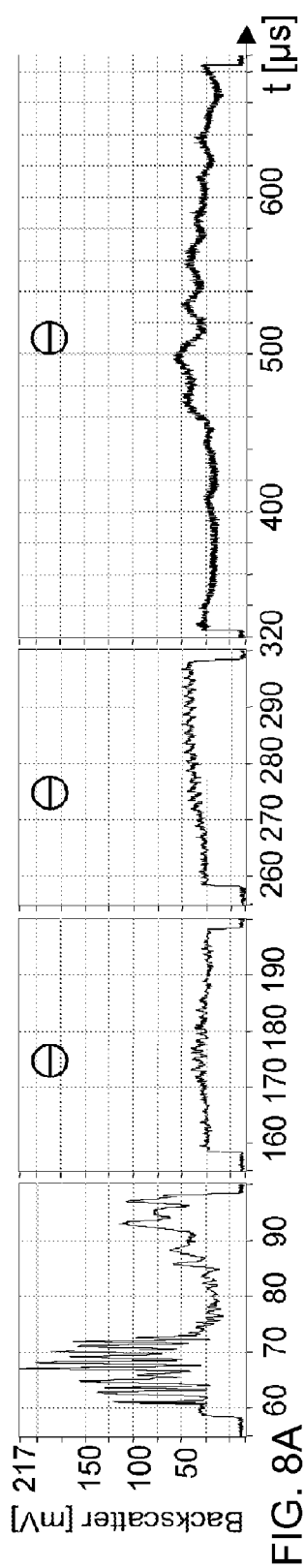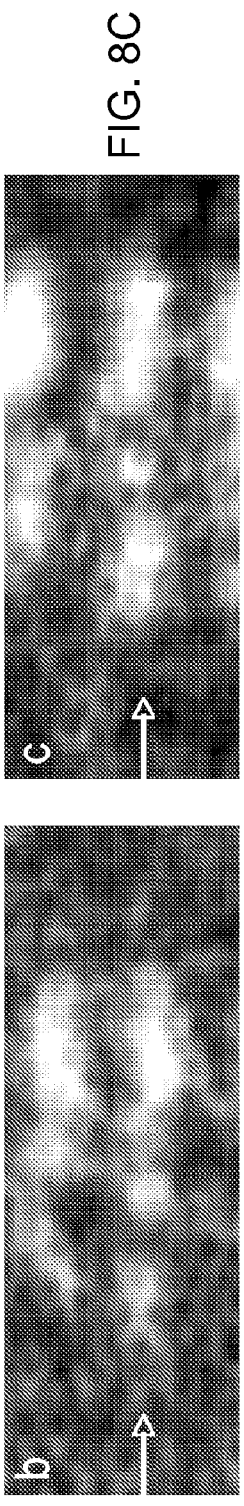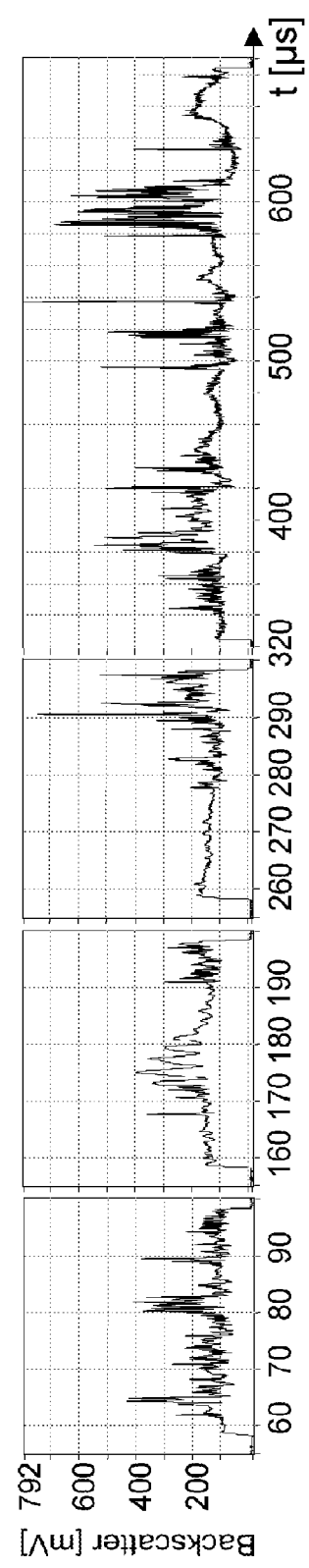

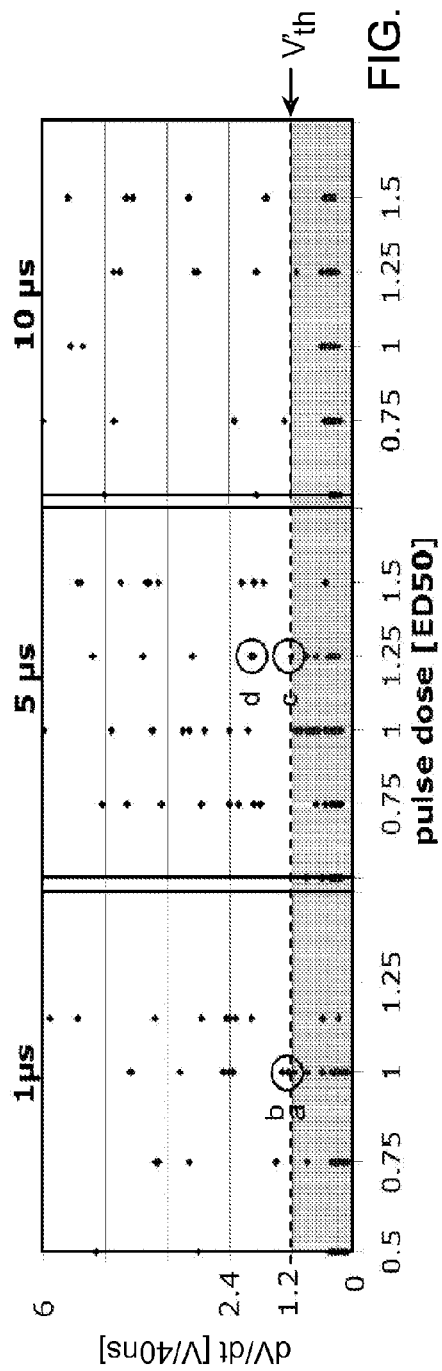
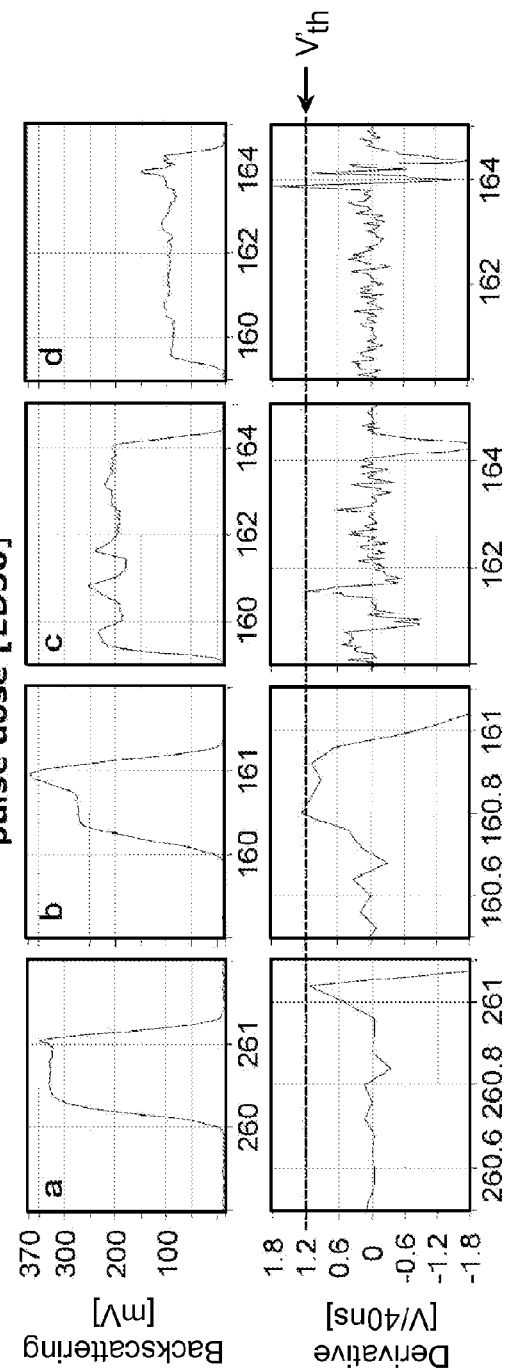
FIG. 12A FIG. 12B FIG. 12C FIG. 12D FIG. 12E

DOSE DETERMINATION FOR INDUCING MICROCAVITATION IN RETINAL PIGMENT EPITHELIUM (RPE)

CROSS-REFERENCE TO RELATED APPLICATIONS

This application is the national stage of International Application Number PCT/US2010/021811, filed on Jan. 22, 2010, which claims priority to U.S. Provisional Patent Application No. 61/146,750, filed on Jan. 23, 2009, the entire contents of each of which are incorporated herein by reference in their entireties.

TECHNICAL FIELD

This disclosure relates to ophthalmic treatment devices, and more particularly to phototherapeutic devices.

BACKGROUND

Selective retina therapy (SRT) is a laser treatment modality for those retinal diseases that are thought to result from a dysfunctional retinal pigment epithelium (RPE). Examples of such diseases include diabetic macular edema, central serous retinopathy and drusen (commonly associated with early AMD).

The laser used in SRT applies a train of green microsecond pulses to the retina. Most of the laser light (≈50%) is initially absorbed by the RPE cells that are loaded with melanosomes; about 7% of the incident light is absorbed in the photoreceptors.

According to the principle of selective photothermolysis, one can selectively destroy tissue and avoid harming adjacent structures by choosing a wavelength that is preferentially absorbed by the target tissue and illuminating the tissue using that wavelength with a pulse that is shorter than the thermal relaxation time of the absorber.

The RPE is an ideal model to test the accuracy of selective targeting because it strongly absorbs visible light (due to its high content of melanosomes) and is surrounded by sensitive but less absorbing neural tissue. The thermal relaxation time of a single melanosome ($TRT_{mel}$) is only about 0.4 µs, while the thermal relaxation time of an RPE cell ($TRT_{RPE}$) is over an order of magnitude longer, or about 5 µs. Because the pulse duration in SRT is on the order of $TRT_{mel}$ and shorter than $TRT_{RPE}$, heat diffusion away from the RPE cells into the neural retina is minimized. As a result, photoreceptors can be preserved.

It has been shown that, following selective destruction of RPE cells, surviving bystander cells cover the lesion within 7-14 days. The therapeutic benefit is thought to arise from the recovery of RPE cells, where new RPE cells are capable of removing existing drusen or edema.

The lasers that create the necessary pulse energy and pulse structure in SRT are large and complicated devices that may be difficult to implement in a clinical setting. Therefore, practical scanning SRT systems use a CW laser, rather than a pulsed laser. In such systems, a scanner rapidly moves the spot of a CW laser over the retina to produce microsecond-long exposure at each irradiated RPE cell. The spot diameter of the scanning device is about the size of one RPE cell (≈15 µm). By adjusting the scanning speed and scan pattern, one can control the extent of damage. For example, by adjusting the settings to minimize heat diffusion into adjacent tissues, one can selectively damage individual RPE cells. By changing the settings to facilitate heat diffusion into adjacent layers, one can instead carry out conventional thermal coagulation of neural retina.

In both, scanning and pulsed SRT, lesions are generally not visible in slit lamp examination. Therefore, the clinical endpoint associated with conventional retinal laser photocoagulation, the whitening of the retina due to thermal coagulation, is not available. Instead, one typically waits an hour after treatment to verify treatment success. The lack of any real-time feedback mechanism carries the risk of unsuccessful treatment, which would require re-treatment. However, the lack of real-time feedback also carries the risk of over-treatment by accidentally exceeding the RPE cell damage threshold of an individual patient. This over-treatment can result in collateral retinal damage and laser scotoma. Consequently, an alternative feedback mechanism that evaluates treatment outcome during the irradiation is desirable for eventual clinical application.

RPE cell damage in SRT was originally thought to be accomplished by thermal necrosis. Over the past years, it has been shown that rapid heating of melanosomes by nano- or microsecond pulses can lead to formation of microscopic bubbles. Vaporization associated with cavitation is initiated when the surface temperature of the melanosome reaches about 150° C. The cavitation extends to a size of a few micrometers around the absorbing melanosome and typically collapses within 1 µs.

SUMMARY

In one aspect, the invention features methods for controlling an irradiation system for selective targeting of RPE cells within a treatment region of the RPE. The methods include depositing a selected amount of energy, e.g., with a laser, on a test region of the RPE; (b) determining an extent to which microcavitation has occurred in the test region; and (c) on the basis of the determination, either depositing the selected amount of energy on the treatment region, or depositing an increased amount of energy, e.g., with a laser, on the test region, and repeating steps (b) and (c).

In one embodiment, depositing a selected amount of energy includes depositing the selected amount of energy on each of a plurality of test spots within the treatment region.

In another embodiment, determining an extent to which microcavitation occurs includes evaluating a derivative of a backscatter signal. Among these practices are those in which determining an extent to which microcavitation has occurred in the test region includes comparing the evaluated derivative with a threshold rate-of-change. In some of these practices, the threshold rate-of-change is selected to indicate the presence of intracellular microcavitation.

In another aspect, the invention features methods for controlling an irradiation system for selective targeting of RPE cells within a treatment region of the RPE. Such a method includes depositing (e.g., using a laser) a selected amount of energy on a test spot on the RPE; receiving, from the RPE, a backscatter signal representative of backscattering from the test spot as a function of time; evaluating a rate-of-change of the backscatter signal; and at least in part on the basis of the evaluated rate-of-change, adjusting the amount of energy deposited on the test spot.

Various embodiments of the invention include those in which illuminating a test spot on the RPE includes, for each of a plurality of discrete test spots: directing a pulsed light source (e.g., a pulsed laser) to point to a test spot on the RPE; and causing a pulse of light to illuminate the test spot, and those in which illuminating a test spot on the RPE includes scanning a CW laser beam across a scan line; and preventing light from reaching selected portions of the scan line.

Among other embodiments are those in which evaluating the rate-of-change includes evaluating a derivative of the backscatter signal.

Embodiments of the invention include those in which adjusting the amount of energy deposited on the test spot includes causing a cessation of energy deposition on the test spot, changing a power level of the laser, or changing a duration of energy deposition on the test spot.

Other embodiments of the invention include depositing a selected amount of energy on the treatment region of the RPE, the selected amount being based on the adjusted amount deposited on the test spot.

In yet other practices, evaluating the rate-of-change of the backscatter signal includes: comparing the rate-of-change of the backscatter signal to a threshold rate-of-change, the threshold rate-of-change being selected to be indicative of the occurrence of microcavitation on the RPE; and determining an inequality relationship between the rate-of-change of the backscatter signal and the threshold rate-of-change.

In some embodiments, the test spot is selected to be outside the treatment region of the RPE, whereas in others, the test spot is selected to be within the treatment region of the RPE.

In another aspect, the invention features methods for controlling an irradiation system for selective targeting of RPE cells within a treatment region of the RPE. Such methods include depositing a first selected amount of optical energy on each of a plurality of test spots on the RPE; for each of the plurality of test spots, determining whether microcavitation has occurred at that test spot; determining a first number representative of the number of test spots at which microcavitation has occurred; determining a first inequality relationship between the first number and a second number, the second number being representative of a threshold number of spots; and at least in part on the basis of the inequality relationship, depositing the first amount of energy on a treatment spot within the treatment region of the RPE.

Various embodiments of the invention include those in which determining the first number includes determining a percentage of test spots at which cavitation occurs, and those in which determining a first inequality relationship includes determining that a percentage of test spots at which microcavitation has occurred is greater than a threshold percentage.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 7A-7D are representations of microscope photos and graphs that show backscattering signals collected during experiments carried out using the apparatus shown in FIG. 1 and the scan pattern of FIG. 4.

FIGS. 8A-8D are representations of microscope photos and graphs that show backscattering signals collected during experiments carried out using the apparatus shown in FIG. 1 and the scan pattern of FIG. 4.

FIGS. 12A to 12D are graphs that show backscatter signals and corresponding maximum derivative values obtained during experiments conducted with the apparatus of FIG. 1.

FIG. 12E is a graph showing the maximum derivatives of 1, 5 and 10 µs pulses at multiples of the $ED_{50FLA}$.

Like reference symbols in the various drawings indicate like elements.

DETAILED DESCRIPTION

U.S. Pat. No. 7,115,120, the contents of which are incorporated herein by reference, discloses the use of optical methods for detecting the onset of cavitation. Specifically, a photodetector detects a backscatter signal from the tissue. Since tissue in which cavitation occurs is more reflective, one can use the magnitude of the backscattering signal as a basis for determining the onset of cavitation.

A difficulty with known methods of detecting cavitation arises from their reliance on human intervention. The clinically observable indications of cavitation are often subtle and can vary significantly from one patient to the next. Thus, the known methods are difficult to automate in part because it is difficult to identify and program any bright-line rule to reliably detect the onset of cavitation.

Identification of bubble formation by manual examination is insufficient for cavitation detection in a clinical setting. Rather, a computer algorithm that alerts the ophthalmologist to the existence of cavitation is preferred. A method to test the local threshold in an irradiation site by using small test spots prior to application of therapeutic irradiation to a large area could also be beneficial.

Figure 1:
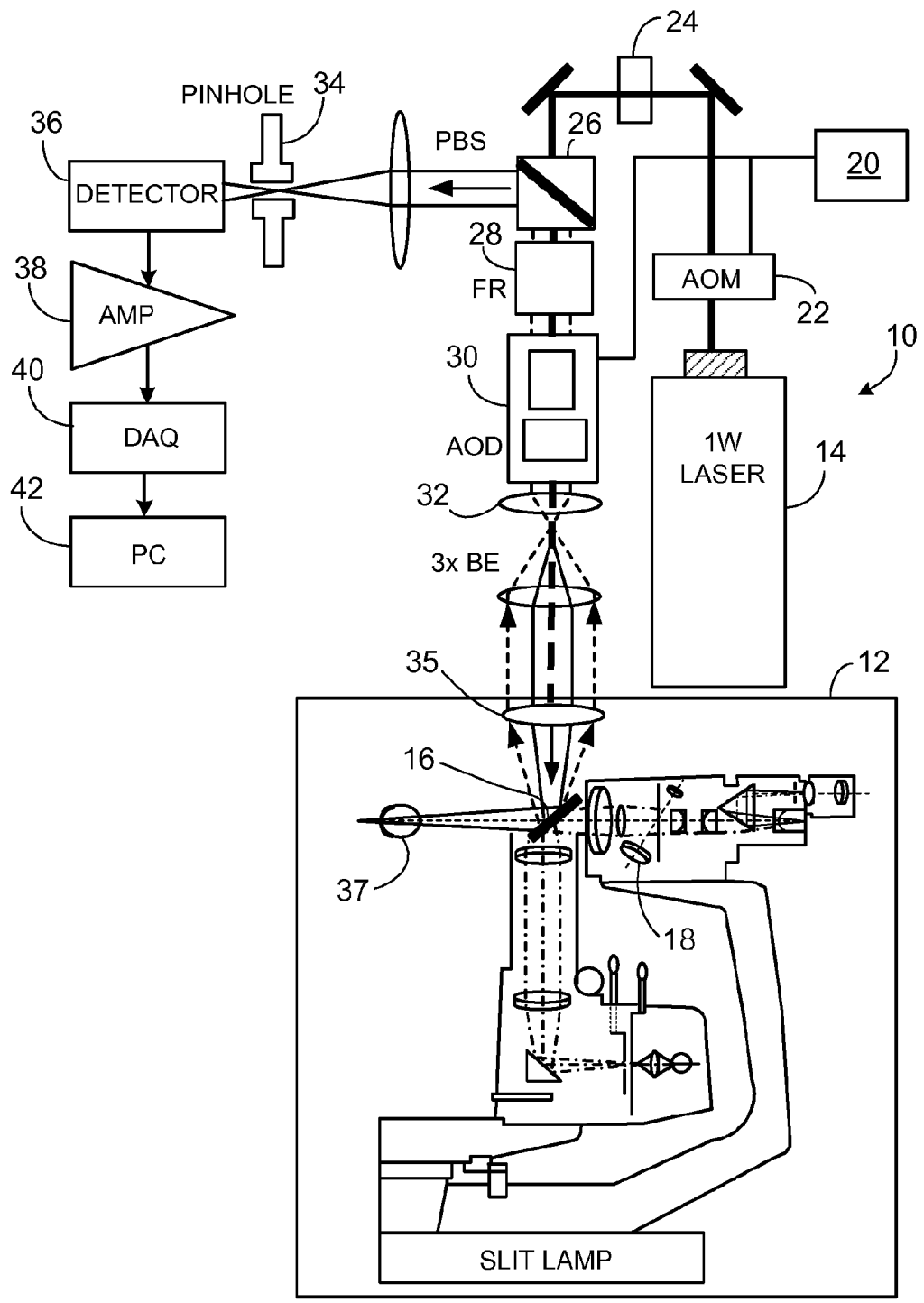
FIG. 1 is a diagram of an apparatus for causing and detecting microcavitation in the RPE.

As shown in FIG. 1, a scanning system 10 for in vivo illumination of the RPE with laser light is assembled on top of an ophthalmic slit lamp 12. By placing a continuous wave (CW) laser 14 and all optical and mechanical components on the slit lamp 12, one avoids the need for fiber delivery. A mirror 16 disposed in front of the objective lenses 18 of the slit lamp 12 aligns the laser beam on a collinear path with the slit lamp's optical axis. The scanner system 10 preserves all the slit lamp's degrees of freedom. Its focal plane is carefully aligned to coincide with the slit lamp's imaging plane. As a result, the slit lamp 12 is configured to be used as a targeting device for the scanning system 10.

In response to instructions from a controller 20, an acousto-optic modulator 22 modulates the collimated output of the laser 14. Polarization of the laser beam is rotated to 45°, for example by a half-wave plate 24. After passing through the half-wave plate 24, the laser light enters a polarizing beam splitter cube 26 and a Faraday rotator 28. The Faraday rotator 28 further rotates the polarization of the beam to produce a horizontal polarization state for an acousto-optic deflector 30 that scans the laser beam in response to instructions from the controller 20. A telecentric post-scanning beam expander 32 then expands the beam by a magnification M. The beam ultimately reaches a focusing lens 35, which focuses it onto the retina 37.

A suitable laser 14 is a 532 nm laser having an output power of 1 W and a beam diameter of 1.6 mm. In one embodiment, the laser 14 is a VENTUS laser manufactured by Laser Quantum of Cheshire, UK, the AOM 22 is a TEM-85-1-0.532 manufactured by Brimrose of Baltimore, Md., and the slit lamp 12 is an SL-130 manufactured by Carl Zeiss of Oberkochen, Germany.

In one embodiment, the acousto-optic deflector 30 is a 2DS-100-35-0.352 manufactured by Brimrose of Baltimore, Md., and the focusing lens 35 is a 125 mm lens, such as the BFPL manufactured by CVI of Albuquerque, N. Mex., which has been v-coated at 532 nm to minimize reflection.

On its return path, the backscattered light of the treatment beam from the retina 37 is collected by the focusing lens 35 and relayed to the telecentric beam expander 32, which now compresses the beam diameter of the backscattered light by a factor of 1/(magnification M) to 5 mm, thereby matching the active aperture of the acousto-optic deflector 30. As a result, backscattered light can be accepted over a larger cross section of the focusing lens 35. Specifically, backscattered light can be collected with a numerical aperture M times the numerical aperture of the treatment beam. This improves photon collection efficiency, which increases in proportion to the square of the numerical aperture. In one embodiment (shown in FIG. 1), the beam diameter is expanded by a factor of M=3 from 1.6 to 4.8 mm in diameter for the radiation light; the corresponding irradiation numerical aperture is about 0.02. Because of the decompression 1/M=1/3, backscattered light can be accepted across a 15 mm diameter. This results in a collection numerical aperture of 0.06, which in turn results in is an increase in photon collection efficiency by a factor of 9.

The backscattered light is then de-scanned in the acousto-optic deflector 30 and passed again through the Faraday rotator 28. This results in a 90° polarization mismatch between the treatment radiation and the backscattered light in the polarizing beam splitter cube 26. The polarizing beam splitter cube 26 then directs the backscattered light onto a confocal pinhole 34, which leads to a photodetector 36, such as a photodiode, an avalanche photodiode, or a photomultiplier tube. The output voltage of the photodetector 36 is amplified by an amplifier 38 and sampled by a data acquisition unit 40 for ultimate storage in a tangible form on a computer-readable medium 42.

In one embodiment, the confocal pinhole 34 is a 100 μm diameter pinhole that leads to an avalanche photodiode 36, such as the C5460 manufactured by APD of Hamamatsu, Japan, the data acquisition unit 40 is a Gage 1250 card manufactured by CompuScope of Lachine, Quebec, and the controller 20 for controlling the AOM and AOD is an arbitrary two-channel function generator, such as the AFG 320 manufactured by Teletronix of Beaverton, Oreg.

In a scanning system 10, the amount of energy deposited on a particular location in the RPE is controlled to ensure that heat generated as a result of laser energy absorbed at a particular location does not spread significantly into adjacent locations. A suitable amount of energy to be deposited at a location is that required to cause microcavitation. As a result, the reliable detection of microcavitation is a desirable feature of the scanning system 10.

Because of its transient nature, microcavitation results in a transient increase in backscattering from the RPE. However, measurement of the backscattering does not lend itself to objectivity and often requires the subjective assessment of a clinician. To avoid these disadvantages, the controller 20 implements a procedure for relying on the rate of change of backscattering with respect to time. Such an algorithm depends on the time derivative of the backscatter signal, or any estimate or approximation thereof, such as a numerically determined slope of the backscatter signal.

Reliance on the rate of change of the backscatter signal, rather than on the signal itself, eliminates variation in signal amplitude, which depends on both the instantaneous laser power and on tissue backscattering. The latter is difficult to compensate for because it can vary not only across different patients but also across different areas within one eye. Because the cavitation bubble grows rapidly (bubble lifetime is on the order of 100 ns) the intensity between two sequential data points changes rapidly. Thus, the rate of change of backscattering provides a more prominent marker of the onset of microcavitation.

A measurement of the rate of change of a backscatter signal delivers large slope values that can be compared against a threshold. Theoretically, a backscattering signal without cavitation has a flat derivative (slope value $V'=0$ V/s) while a signal with cavitation has some maximum slope value $V'>0$ V/s. In practice, system noise causes non-cavitation signals to have a range of derivative values. Nevertheless, backscattering signals associated with cavitation have a significantly larger derivative than signals associated with system noise. Moreover, derivatives of cavitation-related signals are separated from derivatives of non-cavitation-related signals by a gap. Thus, one can readily define a threshold slope value $V'_{th}$ that reliably distinguishes cavitation from non-cavitation signals (FIG. 12). In particular, traces with $V'>V'_{th}$ are likely to be cavitation signals, while traces with $V'<V'_{th}$ are dominated by system noise. With the instrument shown in FIG. 1 a threshold slope value $V'_{th}$ of at least 1.2 V/40 ns is suitable.

Figure 2:
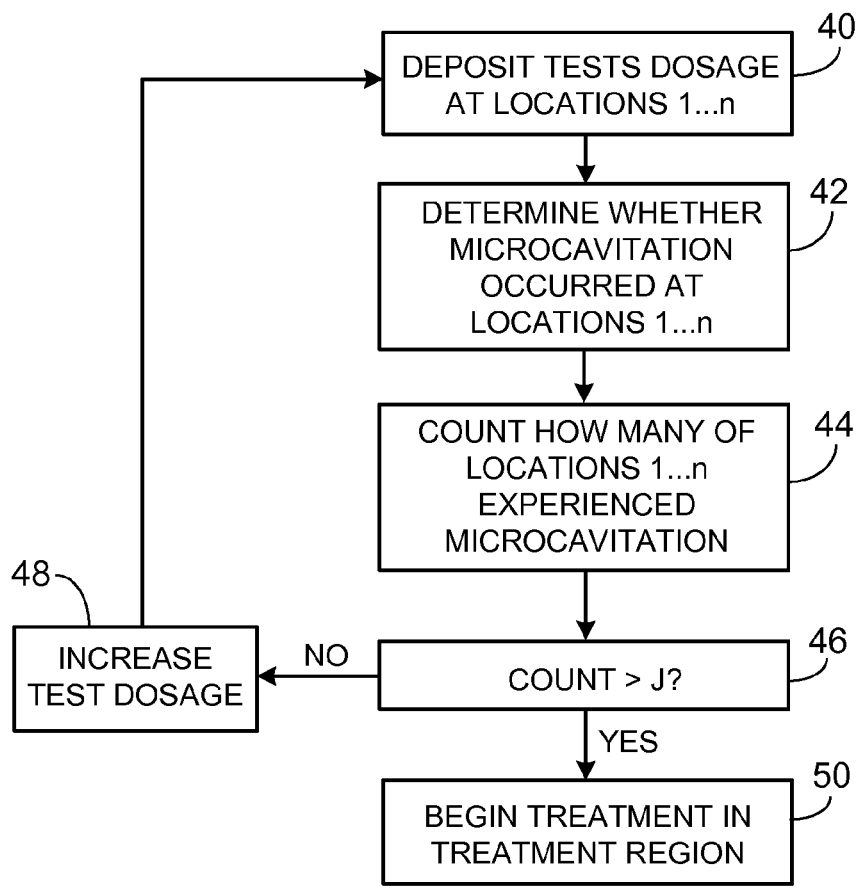
FIG. 2 is a flow-chart of a procedure carried out by the apparatus in FIG. 1.
Figure 3A:
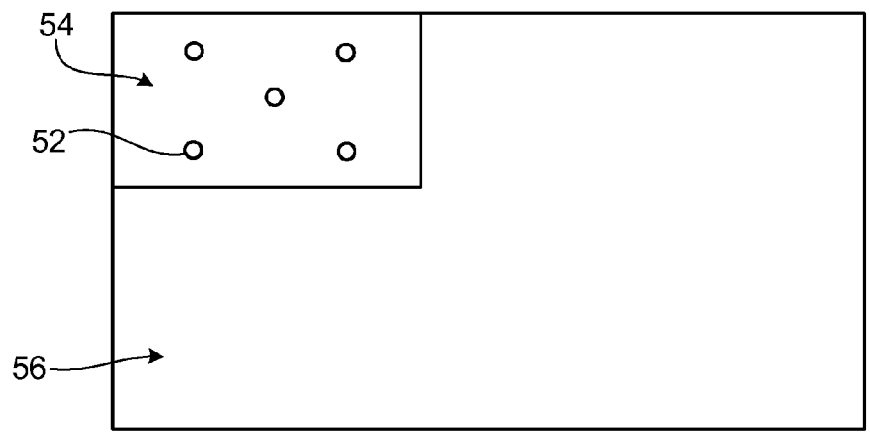
FIGS. 3A-3C are diagrams of test spots in a test region and scan lines in a treatment region, both of which are caused by the apparatus of FIG. 1.
Figure 3B:
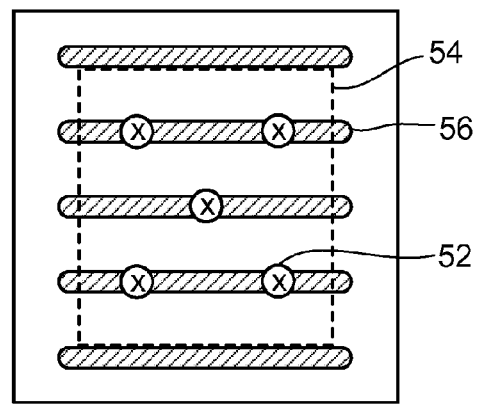
Figure 3C:
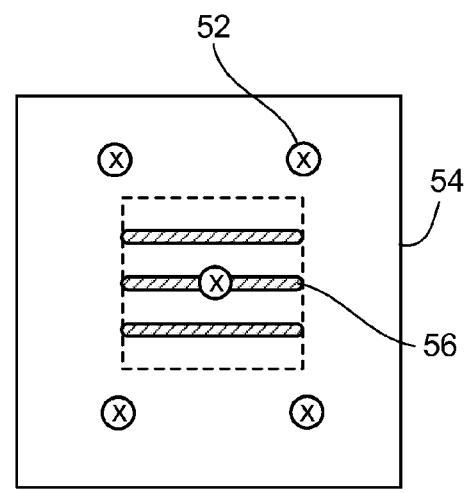

In one practice, shown in FIG. 2, the system determines the correct dosage by causing the laser to deposit a selected amount of energy, referred to herein as "test dosage," on each of a plurality of test spots, or locations (step 40). The plurality of test locations can all be within a test region, or they can be scattered about the treatment region. In one particular practice, shown in FIGS. 3A to 3C, there are five test locations 52 disposed on a square test region 54 in a pattern similar to that found on a playing die. The test region 54 can be adjacent to a treatment region 56, as shown in FIG. 3A, or it can overlap the treatment region, as shown in FIGS. 3B and 3C. In the latter case, the treatment region 56 can encompass the test region 54, as shown in FIG. 3B, or the test region 54 can encompass the treatment region 56 as shown in FIG. 3C.

Referring back to FIG. 2, for each test location 52, the controller determines whether microcavitation has occurred (step 42). The determination can be carried out by using the derivative of the backscatter signal.

The controller then counts how many of the test locations exhibited microcavitation (step 44). If that number is below a predetermined percentage of test locations J selected to indicate a laser dose that is statistically sufficient to kill a desired percentage of targeted cells (step 46), the controller increases the test dosage (step 48) and repeats the procedure.

On the other hand, if the number of test locations 52 that exhibited microcavitation is in excess of the predetermined percentage J, the controller 20 recognizes that the dosage is adequate for treatment. In that case, the controller 20 causes the beam to move into and treat the treatment region 56 (step 50). Treatment can be performed by continuously scanning the laser beam, thereby forming a picket fence of scanlines. Alternatively, treatment can be performed by moving the beam into discrete locations within the treatment region, thereby forming a checkerboard pattern of locations, each of which corresponds to a pulse. In an optional step, during treatment, the controller 20 monitors the derivative of the backscatter signal to confirm that microcavitation of the treatment locations is proceeding as expected.

As disclosed herein, the procedure relies in part on testing to see whether the number of test locations experiencing micro cavitation at a given dosage is in excess of a predetermined percentage. However, one can achieve the same result by other comparisons. For example, one might compare the number of test locations not experiencing micro cavitation to see if that number is less than, rather than greater than, some threshold. Or one might compare reciprocals of these numbers. To encompass these various mathematical manipulations, all of which achieve essentially the same result, the term "inequality relationship" is used to indicate the existence of a value and a threshold, both of which indicate the existence or onset of microcavitation, and both of which are elements of an ordered set of numbers. As such, there will inherently exist an inequality relationship between the value and the threshold, and that inequality relationship can be used as a basis for detecting the onset of microcavitation.

Figure 4:
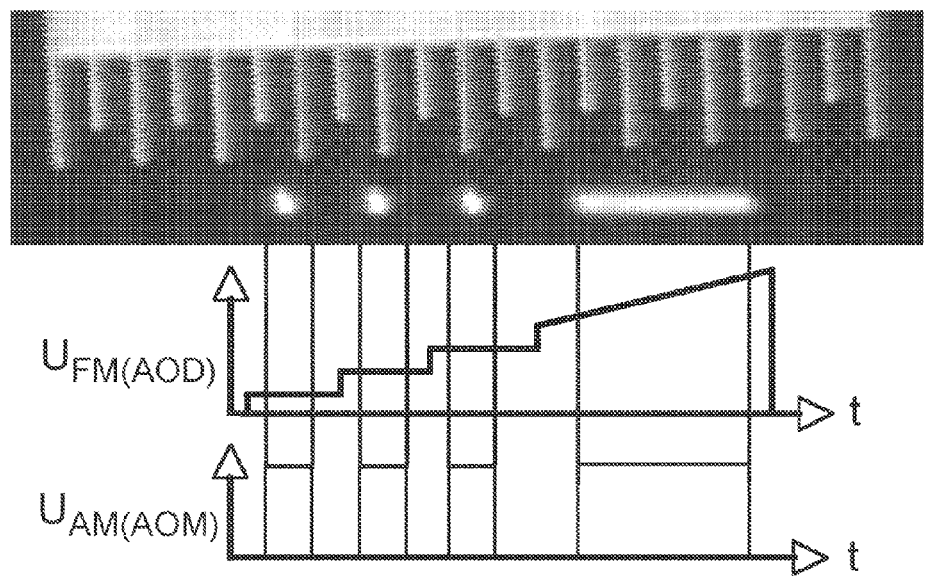
FIG. 4 is an exemplary scan pattern generated by the apparatus of FIG. 1, together with its corresponding control signal, in which test regions and treatment regions are adjacent to each other.

Another example of a scan pattern, shown in FIG. 4, consists of three discretely stepped pulses followed by a continuously scanned line formed by a continuously scanning beam. Shown below the scan pattern in FIG. 4 are waveforms for controlling the acousto-optic modulator 22 and acousto-optic deflector 30 to produce the illustrated scan pattern.

The velocity of the continuously scanning beam is adjusted to match the pulse duration $\tau_p$ of the discretely stepped pulses, i.e. the scan velocity equals one spot diameter per $\tau_p$. This results in all locations receiving the same dosage. An effective way to measure the scan velocity is to pass the spot formed by the scanning beam over the crosshairs of a microscope scale and to detect the transmitted light with a fast photodiode. Since each cross hair of the scale casts a shadow on the photodiode, the time difference between adjacent cross hairs separated by a known distance provides an accurate basis for measuring velocity. Based on this measurement, the controller 20 adjusts the controlling waveform to cause the pulse duration in the test region to be equal to the scanning dwell time in the treatment region 56.

The steps described above in connection with various methods for collecting, processing, analyzing, interpreting, and displaying information can be implemented in computer programs using standard programming techniques. Such programs are designed to execute on programmable computers or specifically designed integrated circuits, each comprising an electronic processor, a data storage system (including memory and/or storage elements), at least one input device, and at least one output device, such as, for example a display or printer. The program code is applied to input data (e.g., measurements of capacitive coupling, measurements of ambient light intensity, and/or measurements of reflected light intensity from objects) to perform the functions described herein. Each such computer program can be implemented in a high-level procedural or object-oriented programming language, or an assembly or machine language. Furthermore, the language can be a compiled or interpreted language. Each such computer program can be stored on a computer or other machine readable storage medium (e.g., CD ROM or magnetic diskette) that when read by a computer or other machine can cause the processor in the computer to perform the analysis and control functions described herein.

EXAMPLES

Experiments were performed in a total of fifteen eyes of eight Dutch belted rabbits. Cell damage and cavitation thresholds were measured in twelve eyes. Rabbits were anesthetized with a mixture of Ketamine and Xylazine (30-40 mg/kg+6-20 mg/kg) by intramuscular injection in the hind legs. The pupils were dilated with Tropicamide 1%, and subsequently with Phenylephrine 5%. A 25G ½" butterfly was inserted into the ear vein for injection of fluorescein. Each rabbit was placed in a holder system that allowed rotation and tilt of the animal with respect to the slit lamp. An ophthalmic Goldmann contact lens was placed on the rabbit's eye, using methylcellulose 2% as contact gel, and held in place by a flexible telescopic arm. The corneas of non-treatment eyes were protected by applying the ophthalmic contact gel, methylcellulose 2%, and a contact lens.

Under slit lamp examination, six marker lesions, purposely coagulating the neural retina, were placed in the fundus using five adjacent lines of slow continuously scanning laser exposure (~100 mW) to allow proper orientation and field determination. The test scan patterns were then placed in columns between the marker lesions at various laser powers. Each scan pattern was applied only once to each irradiation site. The pulse duration and scanning speed were adjusted such that each spot within the exposed area was irradiated for 1, 5, 10, 20, and 40 µs. One parameter was tested per eye. One eye of each rabbit was treated per day; the other eye was treated two days later. Each parameter was tested in at least two eyes of different rabbits, to account for inter-subject variability.

During each irradiation, the backscattering from the retina was recorded simultaneously and analyzed in post-processing to determine whether bubble formation occurred within the RPE. The location of each applied scan pattern and the applied laser power were carefully recorded to enable correlation of backscattering signals with individual exposures.

Immediately after each irradiation, the fundus was examined for whitening that indicates thermal coagulation of the neural retina. Test lesions that became visible immediately after exposure were noted as ophthalmoscopically visible. The test field of the fundus was imaged with a color digital camera mounted on the slit lamp, and captured on a computer.

The rabbit fundus was examined 45 minutes after irradiation with reflectance imaging and fluorescein angiography using a scanning laser ophthalmoscope (SLO; HRA2, Heidelberg Engineering, Heidelberg, Germany). High-resolution reflectance images at 488 nm were acquired to reveal possible morphological changes in the retina that may not have been visible in slit lamp examination. Fluorescein angiography (FLA) is the current standard for detecting laser-mediated damage to the distal blood-ocular barrier, which consists of the RPE and Bruch's membrane and separates the retina from the vasculature of the choroid. In regions where RPE cells have been damaged by the laser exposure, the blood-occular barrier will be compromised and fluorescein can leak into the subretinal space. For fluorescein angiography, a bolus of 1 ml of 10% fluorescein sodium (diluted 1:3 in phosphate buffered saline) was injected into the ear vein of the rabbit via the butterfly. The fluorescein leakage was recorded for evaluation and documentation.

Figures 5A, 5B, 5C:
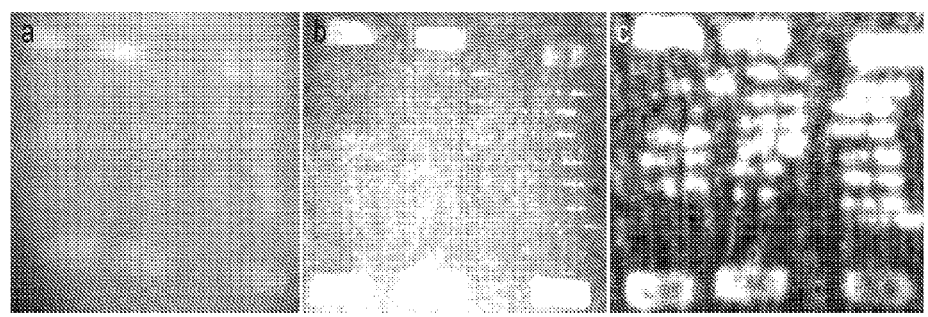
FIGS. 5A-5C are representations of microscope photos that show results of fundus examination after exposure to laser light using the apparatus of FIG. 1 and the scan pattern of FIG. 4.

For data analysis, the scan pattern was treated as two distinct entities, i.e. the pulsed and continuously scanned portions of the scan pattern were evaluated separately. FIG. 5A shows the fundus in rabbits following a 20 μs exposure. Retinal whitening that was visible in slit lamp examination immediately after the exposure marked the ophthalmoscopically visible endpoint. Similarly, high-resolution reflectance imaging showed lesions from pulsed and scanned irradiation in FIG. 5B as sharp white structures. The visibility of lesions in reflectance imaging is likely due to morphological changes that may not be strictly confined to RPE cells.

The visibility of a lesion in the fluorescein angiogram indicated the cell damage or angiographic endpoint (FIG. 5C). FIG. 5C is a fluorescein angiogram showing lesions not visible in FIGS. 5A and 5B. These lesions, which are in the middle and left columns of FIG. 5C and which are visible in neither the reflectance nor slit lamp images, are the desired selective lesions.

The backscattering raw traces for each individual exposure were examined for the presence of a transient voltage increase that represents the endpoint for cavitation. Cavitation was correlated with cell death to identify how frequently cell death is associated with bubble formation. In addition, the raw traces were differentiated to both aid in the determination of bubble formation and to explore the possibility of automated cavitation detection.

Endpoints were evaluated using the probit method. In probit analysis, the lognormal fit through binary response data ("1" for success, "0" for no success) is calculated and the cumulative density distribution of the percentage of targets that do respond to an applied dose is plotted versus the dose. Thus, probit analysis was performed to determine both the probability distribution as a function of laser power and the effective dose 50% ($ED_{50}$) for each parameter and endpoint. The $ED_{50}$ describes the dose required to accomplish an endpoint with a probability of 50% and is commonly referred to as the threshold. Response data were set equal to '1' for each individual cell in the pulsed portion of the scan pattern when the respective endpoint had been reached, while for evaluation of the continuous scans occurrence of the endpoint was indicated anywhere within the scan line. Thus, the pulsed portion of the scan field was treated as three individual events and the continuous scan portion as one individual event. Data analysis was based on a total of 1149 pulses and 383 continuous scans.

The threshold radiant exposure was computed from the corresponding threshold power for each endpoint. For pulses, the radiant exposure is the incident power multiplied by the pulse duration and divided by the area of the laser spot on the retina. For the continuous scan, the radiant exposure H was determined on the scan axis as previously described by $$H = \sqrt{\frac{2}{\pi}} \cdot \frac{2 \cdot P \cdot \tau}{d_0^2}$$

where P is the incident power, τ is the dwell time and $d_0$ is the spot diameter.

A safety margin above the angiographic threshold can be important in selective targeting. This margin is commonly referred to as the therapeutic window and is defined as the ratio of the doses that lead to 15% probability of ophthalmoscopically visible retinal whitening ($ED_{15Ophth}$) and the 85% probability of angiographically visible cell death ($ED_{85FLA}$) ($TW = ED_{15Ophth}/ED_{85FLA}$).

Results

Selective RPE cell damage was accomplished in vivo in experimental rabbits for most parameters. Cavitation was detected routinely by monitoring the backscattering of the treatment laser beam. Cells were damaged predominantly by cavitation with exposures equal or shorter than $TRT_{RPE}$. The number of cells killed without detected cavitation increased with exposure duration.

The setup generated a scan pattern comprised of three discretely stepped pulses, spaced about 110 μm apart in air, followed by a continuously scanned line that was 200 μm long, as illustrated in FIG. 4. It has been shown that the use of a Goldman contact lens on a rabbit eye demagnifies all distances by a factor of 0.66. Therefore, the spacing between pulses and the length of the scan line were calculated to be about 75 μm and 130 μm on the retina, respectively. The scan speed was measured in air to be within 10% of the corresponding pulse duration.

Figure 6:
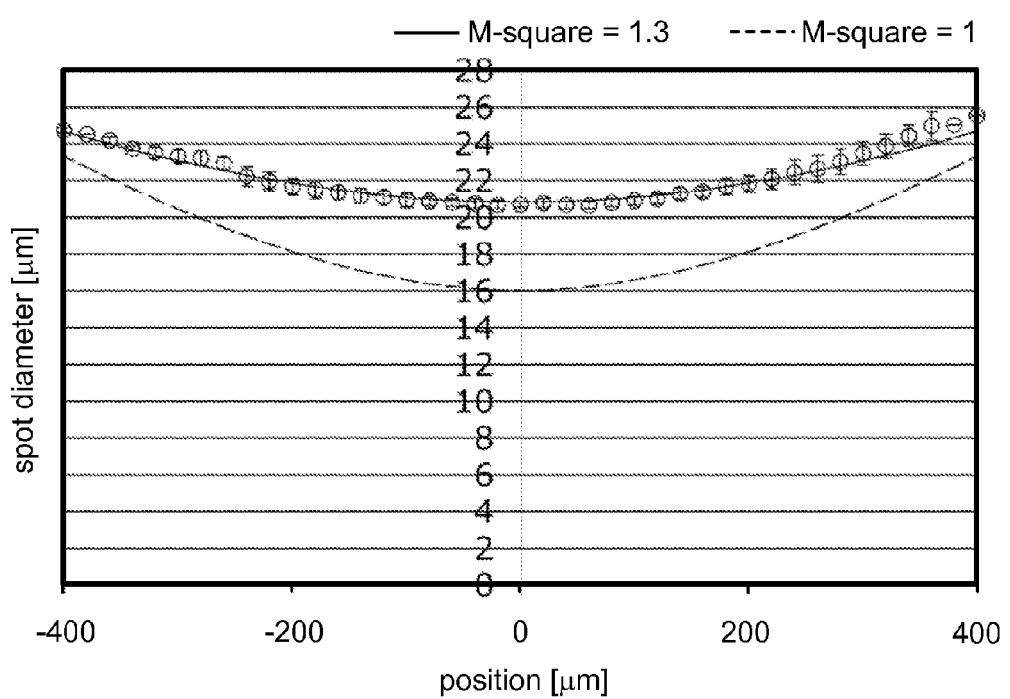
FIG. 6 is a graph that shows spot diameter as a function of position around the focal plane of the apparatus shown in FIG. 1.

The use of acousto-optical devices and polarization optics resulted in a maximum power on the cornea of 400 mW. The spot diameter ($1/e^2$) in air was about 21 μm with a time-diffraction-limit-factor $M^2$ of 1.3, corresponding to a retinal beam diameter of about 14 μm. The depth of focus, defined as twice the Rayleigh range (i.e. the distance over which the beam's waist radius increases by a factor of $2^{1/2}$), was 1.3 mm. Experimentally, the beam diameter was measured in air to increase by about 1 μm over a distance of ±200 μm away from the focal plane, as shown in FIG. 6, which shows spot diameter and beam propagation around the focal plane of the scanner. As is apparent from FIG. 6, the $1/e^2$ spot diameter in air was 21 μm, which corresponded to a retinal spot size of 14 μm. Data points and error bars represent the mean and standard deviation of 12 measurements, fitted with an $M^2$ of 1.3. The dotted line represents a fit using $M^2=1$ for comparison.

RPE cell damage was routinely accomplished with laser power on the order of 100 mW as shown in Table 1 below:

TABLE 1

| Exposure time [μs] | Probability Analysis Pulsed Exposure | | | Probability Analysis Scanning Exposure | | | |
|---|---|---|---|---|---|---|---|
| | Cell death [mW] | Cavitation [mW] | RedFree [mW] | Cell death [mW] | Cavitation [mW] | RedFree [mW] | Ophth. [mW] |
| 1 | 354 (1.2) | 332 (1.2) | | 288 (1.3) | 258 (1.4) | | |
| 5 | 96 (1.6) | 94 (1.6) | | 74 (1) | 60 (1.2) | | |
| 10 | 108 (1.8) | 123 (1.7) | | 63 (1.5) | 69 (1.6) | 195 (1.2) | 354 (1.2) |
| 20 | 65 (1.5) | 84 (1.2) | 197 (1.6) | 43 (1.1) | 70 (1) | 113 (1) | 206 (1) |
| 40 | 53 (1.7) | 71 (1.7) | 151 (1.8) | 30 (1.2) | 41 (1.4) | 63 (1.2) | 170 (1.2) |

The probit slope values ($S=ED_{85}/ED_{50}$) account for the width of the probability distributions and ranged from 1.2 to 1.8 for the pulses and from 1 to 1.6 for the scans. Intracellular cavitation was detected as a transient increase in backscattering signal. Cell damage and cavitation threshold powers were about equal in 5 μs pulses and in 10 μs scans. Bleeding in the retinal space that would have indicated a rupture of Bruch's membrane was never observed. Lesions were never visible with slit lamp or reflectance examination for 1 and 5 μs exposures, regardless of the irradiation mode. Whitening of the retina, indicating thermal denaturation of the retina, was only observed in continuous scans and never in individual pulses; consequently, the ophthalmoscopic threshold and therapeutic window were only given for scanning exposures.

Intracellular cavitation was detected by monitoring the backscattering from the retina. As an example, for exposure times close to the RPE thermal relaxation time ($TRT_{RPE}$), FIGS. 7B and 7C show two representative fluorescein angiography images with corresponding backscattering traces for 5 μs exposures. FIG. 7B and corresponding backscatter signal in FIG. 7A are below the cell damage threshold. As shown in FIG. 7B, two out of three pulses and the continuous scan line damaged RPE cells at 25% below $ED_{50FLA}$. The corresponding backscattering traces in FIG. 7A show transient increases in detector voltage for all three pulses and within the scan line. Thus, a bubble was detected in the center pulse that was insufficient to damage the cell. FIG. 7C and corresponding backscatter signals in FIG. 7D show results of radiation at about $ED_{50FLA}$. In this case, RPE cells were killed in all three pulses and in a fraction of the scan line, as shown in FIG. 7C. The corresponding backscattering traces show cavitation throughout the pattern, shown in FIG. 7D. In most 1 and 5 μs exposures, cavitation correlated with cell death. Exceptions were due to cavitation being detected in surviving cells.

FIGS. 8A to 8D show an example of exposure duration much longer than $TRT_{RPE}$ (40 μs). At threshold, all three pulses and the continuous scan were able to damage RPE cells, as seen by the fluorescein leakage in the fluorescence angiogram, shown in FIG. 8B. However, cavitation was only detected in the first pulse, as shown in the accompanying backscatter signal in FIG. 8A. The three pulses and the scan line successfully damaged RPE cells at 1.5 $ED_{50FLA}$, as shown in FIG. 8C. This is consistent with cavitation in all backscattering traces for this exposure, as shown in the corresponding backscatter signal in FIG. 8D. Overall, dead cells without detected cavitation were found in exposures with duration longer than $TRT_{RPE}$.

Figure 9A:
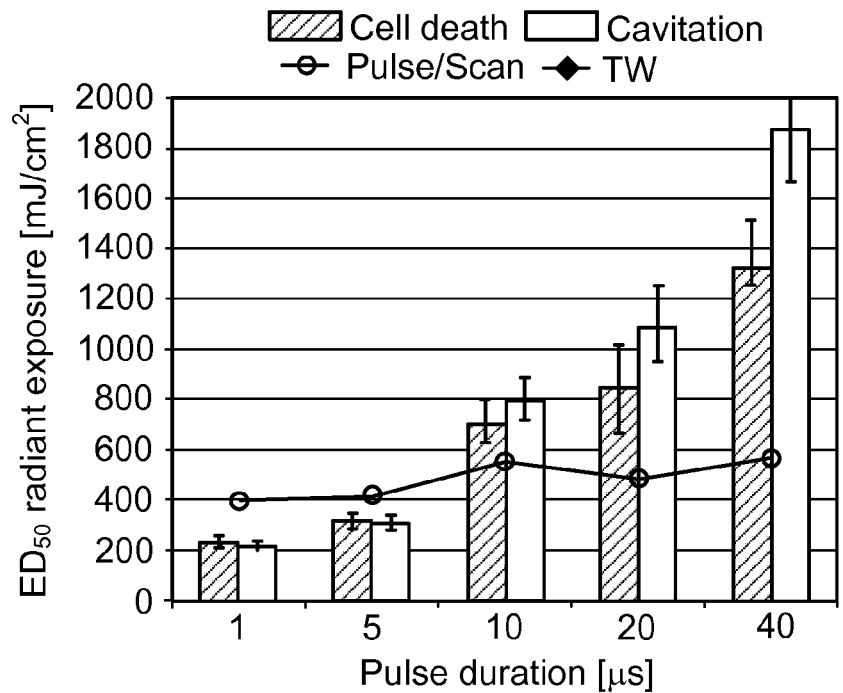
FIGS. 9A and 9B are graphs that show a measured relationship between cell damage and cavitation for pulsed and CW exposure resulting from use of the apparatus shown in FIG. 1.
Figure 9B:
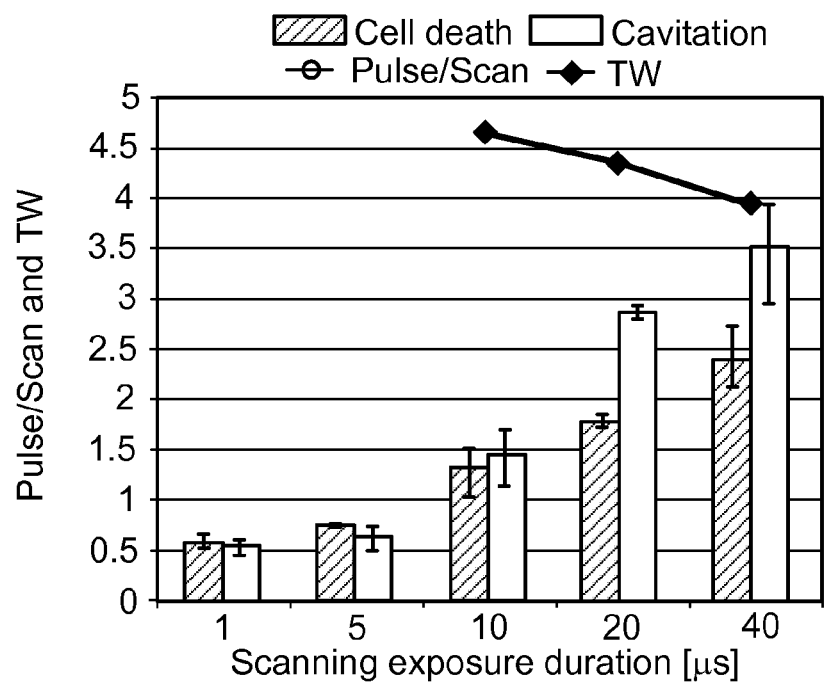

Based on these results, the thresholds for cell damage and cavitation were computed. Both threshold radiant exposures were about equal for 5 μs pulses and increased with exposure duration for both pulses (FIG. 9A) and continuous scans (FIG. 9B). In the continuous scans, the threshold for cavitation was smaller than the cell damage threshold for 1 and 5 μs exposures. Beginning with 10 μs exposures, the cavitation threshold was higher than that for cell damage regardless of the irradiation mode. The thresholds further diverged with increasing exposure duration. Both thresholds increased more sharply for pulsed exposure. As a result, higher radiant exposure was required to damage cells and induce cavitation in pulses as compared to scans in long exposure durations. The ratio of pulsed over scanned $ED_{50FLA}$ was about one for 1 and 5 μs exposures, and diverged with increasing exposure duration to 1.4 with 40 μs exposures.

The therapeutic window, determined by slit lamp examination, was about 4 for 40 μs scans and increased with shorter dwell times (4.6 with 10 μs). Even at the highest available laser power of 400 mW, no retinal whitening was observed for either 5 or 1 μs scans or in any pulses.

Threshold determination alone may not be sufficient, in some embodiments, to identify how frequently cavitation correlates with cell death because both dead cells without detected bubble formation and living cells that endured cavitation contribute to the probability distribution. To identify the correlation between cavitation and cell death, the percentage of dead cells that were associated with cavitation was determined for each parameter and irradiation mode.

Figures 10A, 10B:
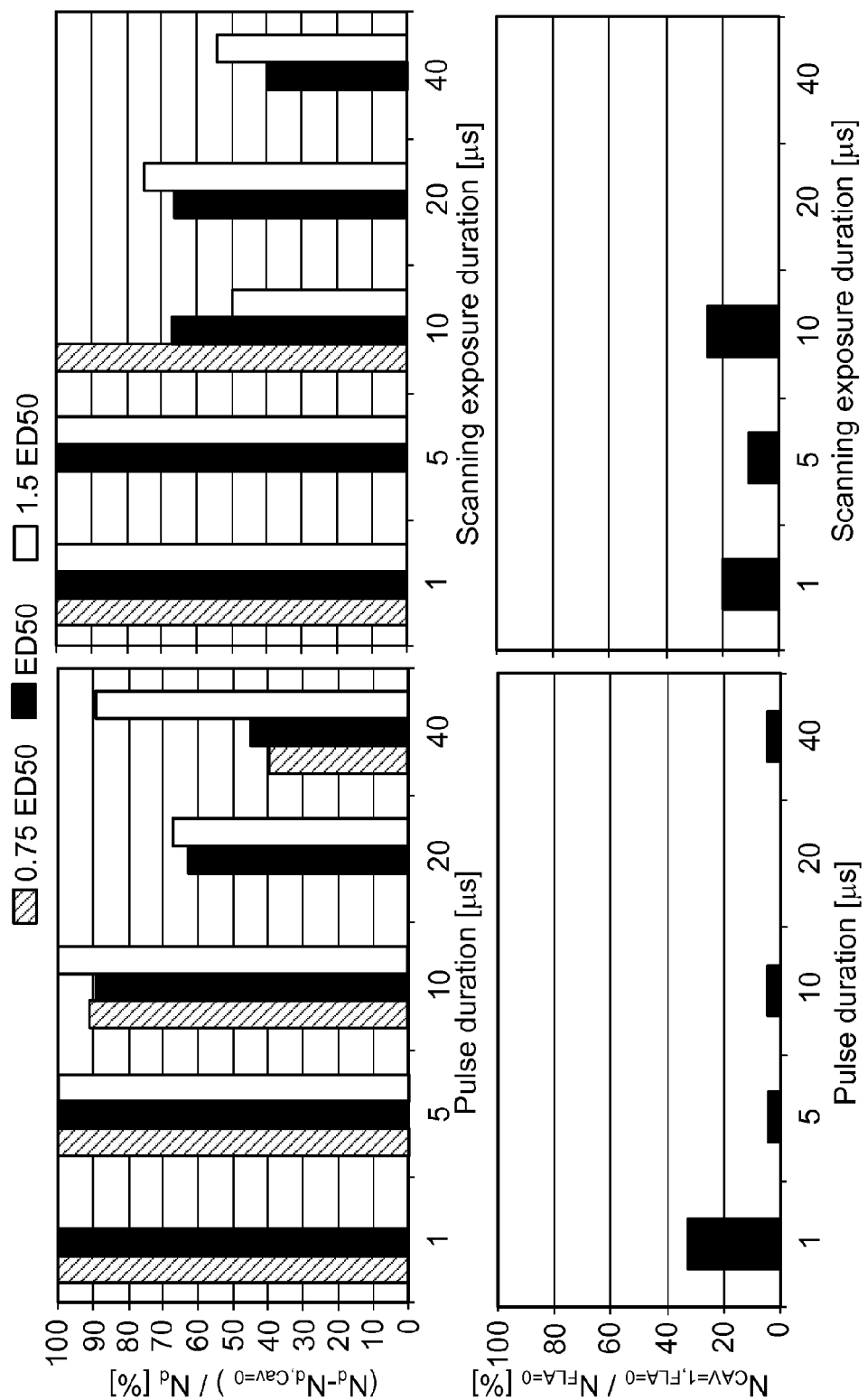
FIGS. 10A and 10B are graphs that show percentages of dead cells and live cells subject to cavitation in an experiment using the apparatus shown in FIG. 1 and the scan pattern of FIG. 4, and indicating the extent to which cavitation correlated with cell death.

As shown in FIG. 10A, cavitation was detected in all dead cells for 1 and 5 μs exposures in a range from 25% below to 50% above cell damage threshold. At $ED_{50FLA}$, the percentage of dead cells accompanied by cavitation decreased with increasing exposure duration to about 40% at 40 μs. Similarly, the percentage of cells that survived a cavitation event was also determined.

As shown in FIG. 10B, as many as 33% of all surviving cells were associated with cavitation in 1 μs pulses. For longer pulses, cavitation was detected in about 5% of live cells. In the scanning portion of the scan pattern, the percentage of cavitation in surviving cells was on the order of 20% and no live cells were associated with cavitation for scans slower than 10 μs.

Figure 11:
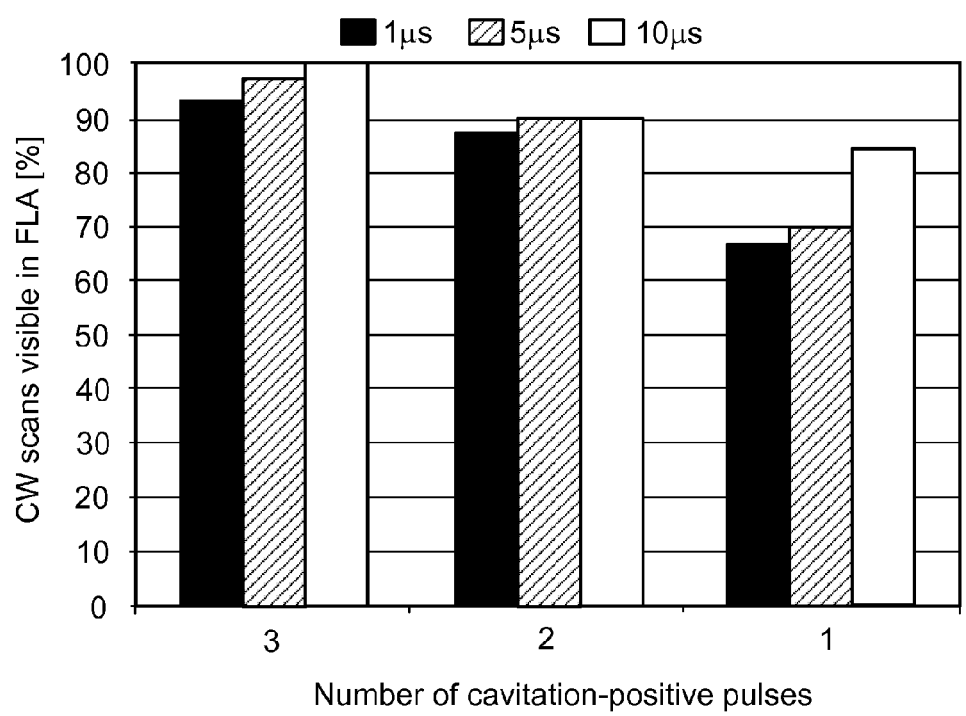
FIG. 11 is a graph that shows the extent to which cavitation detected during pulsed irradiation with three different pulse lengths correlated with cell death during scanning irradiation using the apparatus of FIG. 1 and the scan pattern of FIG. 4.

In order to investigate the relationship between cavitation in pulses and cell death in continuous scans, the percentage of continuous scans that successfully damaged cells was evaluated as a function of cavitation in the pulses of the same pattern. The results are summarized in FIG. 11. As indicated by FIG. 11, if cavitation was detected in all three pulses of the pattern, the continuous scan line killed cells in more than 90% of all trials. The percentage decreased to between 65% and 85% with 1 or 10 μs pulses, respectively, when bubble formation was observed in only one out of three pulses. On the basis of this data, it is reasonable to conclude that test pulses can be used to measure the local threshold in particular test location in a test site before a therapeutic, large-area scan is applied to a treatment location in a treatment site.

The derivative of the backscattering signal traces aided in the determination of bubble formation. FIG. 12E shows the maximum derivatives of 1, 5 and 10 us pulses at multiples of the $ED_{50FLA}$. Maximum derivatives of transient voltage increases due to cavitation ranged from larger than 1.2 V/40 ns to up to 50 V/40 ns; slopes larger than 6 V/40 ns were omitted for clarity. In backscattering traces without cavitation, the derivative was dominated by system noise and was smaller than 1.2 V/40 ns. Thus, cavitation and non-cavitation signals were separated by a threshold value of 1.2V/40 ns.

Most derivatives shown in FIGS. 12A-12D indicate cavitation or no cavitation. Less than 2% of all evaluated derivatives fall within a region of ±0.2 V/40 ns of the threshold. FIGS. 12A-12D show representative backscattering traces with their corresponding derivatives close to the threshold, for 1 and 5 μs pulses, respectively. In FIG. 12A, a backscattering signal with a derivative of 1.16 V/40 ns would be classified as displaying no cavitation. In FIG. 12B, a signal having a derivative of 1.28 V/40 ns would be classified as a signal indicative of cavitation. Both of the 5 μs traces in FIG. 12C and FIG. 12D would be classified as showing cavitation, because their derivatives are 1.2 and 1.8 V/40 ns, respectively.

The feasibility of optically detecting intracellular cavitation during selective targeting of the rabbit RPE has been investigated using the system shown in FIG. 1. The scan pattern generated three discretely stepped pulses followed by a continuously scanned line with clinically crucial exposure durations ranging from 1 to 40 μs. Selective RPE cell damage was accomplished with moderate laser power on the order of 100 mW. The absence of visible lesions both under slit lamp examination and using high-resolution reflectance imaging with an SLO suggests that 1 and 5 µs exposures are safe for selective targeting with a therapeutic window that is at least 5.4 regardless of the irradiation mode.

Intracellular cavitation was detected routinely by monitoring the backscattered light of the treatment laser beam. Cell death was accompanied by cavitation with irradiation on the order of the thermal relaxation time in duration, suggesting that the cell damage mechanism is photo-mechanical for 1 and 5 µs pulses and scans. With increasing exposure time, the cell damage mechanism undergoes a gradual transition to a more photo-thermal mode as an increasing number of cells are killed without detected cavitation. This study confirms in an in vivo model that intracellular cavitation, detected by monitoring the backscattering from the target tissue, can reliably report RPE cell damage for exposure durations of at least up to 10 µs.

Moreover, the derivative of backscattering traces with or without cavitation are separated by a fixed threshold value for all exposure durations and for both irradiation modes. Therefore, a simple computer-based comparator can automatically distinguish between cavitation and non-cavitation based on the maximum derivative of the backscattering traces. Furthermore, cavitation in the pulsed portion of the scan pattern correlates with cell death in the scans. As a result, test pulses can be utilized in a scanner to measure and predict the local cell damage threshold, before a large-area therapeutic scan is applied. The foregoing techniques are applicable to the control of dosimetry for individual irradiation sites in eyes with varying optical characteristics and clarity.

Other Embodiments

It is to be understood that the foregoing description is intended to illustrate and not limit the scope of the disclosure, which is defined by the scope of the appended claims. Other aspects, advantages, and modifications are within the scope of the following claims.

The invention claimed is:

1. An automated method for determining a treatment for retinal pigment epithelium (RPE) cells within a treatment region of the RPE, the method comprising:
   (i) exposing each one of a plurality of test spots on the RPE to a first quantity of treatment radiation from a radiation source;
   (ii) for each one of the test spots in the plurality of test spots, automatically determining whether microcavitation occurred in response to the treatment radiation by:
      (a) measuring a signal corresponding to treatment radiation scattered from the test spot in a direction opposite to a direction along which the treatment radiation is delivered to the test spot;
      (b) determining a rate of change of an amplitude of the measured signal; and
      (c) determining whether microcavitation occurred at the test spot by comparing the rate of change of the amplitude of the measured signal to a first threshold value for the rate of change of the measured signal that corresponds to microcavitation;
   (iii) determining a fraction of the plurality of test spots at which microcavitation occurred in response to the treatment radiation; and
   (iv) comparing the fraction to a second threshold value for the fraction to determine whether the first quantity of treatment radiation is suitable for treating the RPE cells.

2. The method of claim 1, further comprising exposing the RPE cells within the treatment region to a quantity of treatment radiation that corresponds to the first quantity of the treatment radiation if the fraction exceeds the second threshold value.

3. The method of claim 1, further comprising, if the fraction is less than the second threshold value:
   exposing each of the plurality of test spots on the RPE to a second quantity of treatment radiation larger than the first quantity; and
   repeating steps (ii)-(iv) to determine whether the second quantity of treatment radiation is suitable for treating the RPE cells.

4. The method of claim 1, further comprising generating the second quantity of treatment radiation by adjusting at least one of an average output power of the radiation source, and a pulse duration of the radiation source.

5. The method of claim 1, wherein the first threshold value corresponds to the occurrence of intracellular microcavitation in RPE cells.

6. The method of claim 1, further comprising generating the treatment radiation using a pulsed laser.

7. The method of claim 6, further comprising, for each one of the test spots, delivering the treatment radiation in multiple radiation pulses to the test spot.

8. The method of claim 1, further comprising generating the treatment radiation using a continuous wave (CW) laser.

9. The method of claim 1, wherein at least some of the plurality of test spots are within the treatment region.

10. The method of claim 1, wherein each one of the plurality of test spots is outside the treatment region.

11. An automated system for determining a treatment for retinal pigment epithelium (RPE) cells within a treatment region of the RPE, the system comprising:
   a radiation source configured to expose regions of the RPE to treatment radiation;
   a detector configured to measure a signal corresponding to treatment radiation scattered from the RPE in a direction opposite to a direction along which the treatment radiation is delivered to the RPE; and
   an electronic processor configured to:
      (i) direct the radiation source to expose each one of a plurality of test spots on the RPE to a first quantity of treatment radiation;
      (ii) for each one of the test spots in the plurality of test spots, automatically determine whether microcavitation occurred in response to the treatment radiation by:
         (a) receiving a signal measured by the detector corresponding to scattered treatment radiation;
         (b) determining a rate of change of an amplitude of the received signal; and
         (c) comparing the rate of change of the amplitude of the received signal to a first threshold value for the rate of change of the measured signal that corresponds to microcavitation to determine whether microcavitation occurred at the test spot;
      (iii) determine a fraction of the plurality of test spots at which microcavitation occurred in response to the treatment radiation; and
      (iv) compare the fraction to a second threshold value for the fraction to determine whether the first quantity of treatment radiation is suitable for treating the RPE cells.

12. The system of claim 11, wherein the electronic processor is configured to direct the radiation source to expose the RPE cells within the treatment region to a quantity of treatment radiation that corresponds to the first quantity of the treatment radiation if the fraction exceeds the second threshold value.

13. The system of claim 11, wherein the electronic processor is configured so that if the fraction is less than the second threshold value, the electronic processor:
  directs the radiation source to expose each of the plurality of test spots on the RPE to a second quantity of treatment radiation larger than the first quantity; and
  repeats steps (ii)-(iv) to determine whether the second quantity of treatment radiation is suitable for treating the RPE cells.

14. The system of claim 11, wherein the first threshold value corresponds to the occurrence of intracellular microcavitation in RPE cells.

15. The system of claim 11, wherein the radiation source comprises a pulsed laser.

16. The system of claim 15, wherein the radiation source is configured to deliver the treatment radiation in multiple radiation pulses.

17. The system of claim 11, wherein the radiation source comprises a continuous wave (CW) laser.

18. The system of claim 11, wherein the electronic processor is configured to adjust at least one of an average output power and a pulse duration of the radiation source to direct the radiation source to expose a plurality of test spots on the RPE to a second quantity of treatment radiation.

* * * * *

UNITED STATES PATENT AND TRADEMARK OFFICE
CERTIFICATE OF CORRECTION

PATENT NO. : 8,968,280 B2  
APPLICATION NO. : 13/145605  
DATED : March 3, 2015  
INVENTOR(S) : Charles P. Lin, Clemens Alt and Ho Lee Page 1 of 1

It is certified that error appears in the above-identified patent and that said Letters Patent is hereby corrected as shown below:

In the Claims

In column 14, line 14, claim 4, delete "claim 1," and insert -- claim 3, --

Signed and Sealed this
Eleventh Day of August, 2015

Michelle K. Lee
*Director of the United States Patent and Trademark Office*